(12) United States Patent
Sørensen et al.

(10) Patent No.: US 10,287,109 B2
(45) Date of Patent: May 14, 2019

(54) BLOOD SAMPLES TRANSPORT SYSTEM

(71) Applicant: Blak & Sørensen ApS, Bording (DK)

(72) Inventors: Peter Møller Sørensen, Jelling (DK); Daniel Blak, Rødkærsbro (DK)

(73) Assignee: Blak & Sørensen ApS, Bording (DK)

( * ) Notice: Subject to any disclaimer, the term of this patent is extended or adjusted under 35 U.S.C. 154(b) by 8 days.

(21) Appl. No.: 15/546,305

(22) PCT Filed: Feb. 17, 2016

(86) PCT No.: PCT/DK2016/050044
§ 371 (c)(1),
(2) Date: Jul. 26, 2017

(87) PCT Pub. No.: WO2016/131461
PCT Pub. Date: Aug. 25, 2016

(65) Prior Publication Data
US 2018/0029808 A1    Feb. 1, 2018

(30) Foreign Application Priority Data

Feb. 17, 2015    (DK) ................................ 2015 70086

(51) Int. Cl.
*B65G 51/36*    (2006.01)
*B65G 51/02*    (2006.01)
(Continued)

(52) U.S. Cl.
CPC ............. *B65G 51/02* (2013.01); *B65G 51/36* (2013.01); *G01N 35/04* (2013.01); *B65G 51/16* (2013.01);
(Continued)

(58) Field of Classification Search
USPC ..... 406/3, 10, 27, 36, 67, 84, 112, 145, 147, 406/151, 176, 197
See application file for complete search history.

(56) References Cited

U.S. PATENT DOCUMENTS 2,890,913 A * 6/1959 Miskel ..................... B65B 3/006
193/44
3,907,231 A * 9/1975 Kreiner ................... B65G 51/04
406/111
(Continued)

FOREIGN PATENT DOCUMENTS

DE    2165782 A1    7/1972
DE    2221638 A1    11/1973
(Continued)

*Primary Examiner* — Joseph A Dillon, Jr.
(74) *Attorney, Agent, or Firm* — James Creighton Wray; Meera P. Narasimhan

(57) ABSTRACT

A method of transporting blood samples without using a capsule, in a tube system with an internal diameter that is greater than the external diameter of the applied blood samples and lesser than the lengths of the applied blood samples, the method including at least the following steps: •A: a blood sample (8) with an external diameter in the range Ø12 mm to Ø18 mm and with a length in the range from 80 mm to 110 mm is introduced in a tube system (1) that includes a dispatch station (3) and a receiver station (4), •A1: the physical dimensions of the blood sample (8) is checked and it is ensured that the blood sample (8) fits the tube system, •B: the blood sample (8) is dispatched from the dispatch station (3) by means of dispatching air.

15 Claims, 1 Drawing Sheet

(51) Int. Cl.
*G01N 35/04* (2006.01)
*B65G 51/16* (2006.01)
*B65G 51/20* (2006.01)
*B65G 51/28* (2006.01)
*B65G 51/44* (2006.01)

(52) U.S. Cl.
CPC .............. *B65G 51/20* (2013.01); *B65G 51/28* (2013.01); *B65G 51/44* (2013.01); *G01N 2035/0406* (2013.01); *G01N 2035/0481* (2013.01)

(56) References Cited

U.S. PATENT DOCUMENTS

| | | | | |
|---|---|---|---|---|
| 3,945,682 | A * | 3/1976 | Hoagland | B65G 51/02 |
| | | | | 198/402 |
| 3,986,590 | A * | 10/1976 | Lapidus | B65G 51/04 |
| | | | | 193/32 |
| 4,135,685 | A * | 1/1979 | Girshovich | B65G 51/20 |
| | | | | 406/10 |
| 4,343,574 | A | 8/1982 | Anders | |
| 4,480,947 | A * | 11/1984 | Nagasaka | G01F 1/74 |
| | | | | 406/14 |
| 4,684,296 | A * | 8/1987 | Horii | B65G 53/42 |
| | | | | 137/1 |
| 4,976,356 | A * | 12/1990 | Mizuno | B07C 5/02 |
| | | | | 198/345.1 |
| 5,146,166 | A | 9/1992 | Bartuska | |
| 5,641,250 | A * | 6/1997 | Bostelmann | A24C 5/31 |
| | | | | 131/282 |
| 6,626,612 | B2 * | 9/2003 | Knapp | B65G 51/03 |
| | | | | 406/19 |
| 7,424,340 | B2 * | 9/2008 | Owens | B65G 51/46 |
| | | | | 406/182 |
| 8,500,373 | B1 | 8/2013 | Epps | |
| 9,309,063 | B2 * | 4/2016 | Soerensen | B65G 51/02 |
| 9,643,791 | B2 * | 5/2017 | Landler | B65G 21/2054 |
| 9,688,485 | B2 * | 6/2017 | Sorensen | B65G 51/02 |
| 2012/0195698 | A1* | 8/2012 | Soerensen | B65G 51/02 |
| | | | | 406/34 |
| 2016/0152420 | A1* | 6/2016 | Sorensen | B65G 51/02 |
| | | | | 406/191 |

FOREIGN PATENT DOCUMENTS

| | | |
|---|---|---|
| EP | 0516111 A1 | 12/1992 |
| EP | 2483186 A1 | 8/2012 |
| EP | 2620396 A1 | 7/2013 |
| WO | 9735792 A1 | 10/1997 |
| WO | 2014081283 A1 | 5/2014 |

* cited by examiner

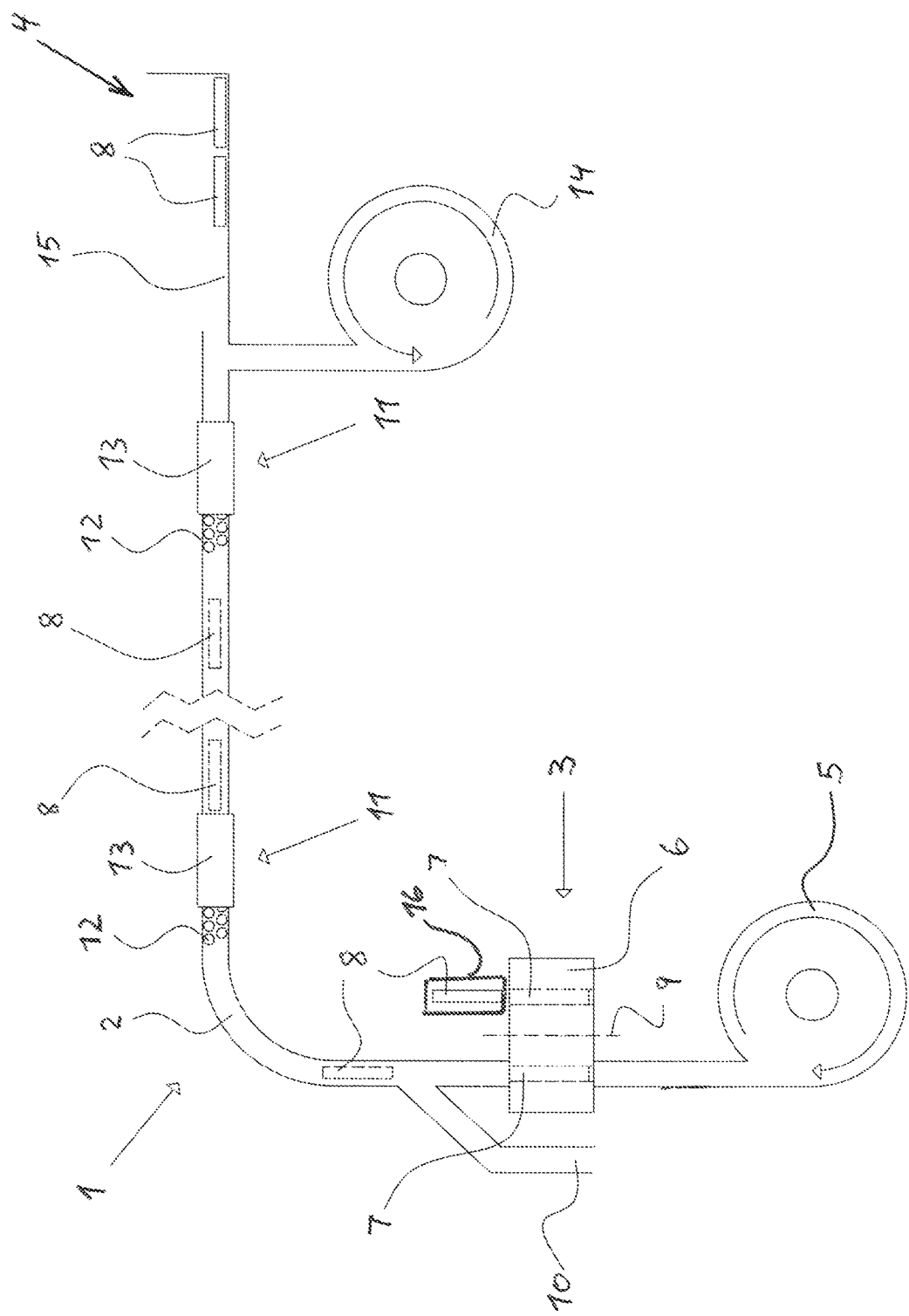

BLOOD SAMPLES TRANSPORT SYSTEM

This application claims the benefit of Danish Application No. PA 2015 70086 filed Feb. 17, 2015, and PCT/DK2016/050044 filed Feb. 17, 2016, International Publication No. WO 2016/131461 A1, and the amended sheets filed with the Demand, which are hereby incorporated by reference in their entirety as if fully set forth herein.

FIELD OF THE INVENTION

The present invention concerns a method for transporting blood samples in a tube system with an internal diameter that is greater than the external diameter of the applied blood samples and lesser than the lengths of the applied blood samples, the method including at least the following steps:
A: a blood sample with an external diameter in the range from Ø12 mm to Ø18 mm and with a length in the range from 80 mm to 110 mm is introduced in a tube system that includes a dispatch station and a receiver station, and wherein
B: the blood sample is sent from the dispatch station by means of dispatching air.
The invention also concerns a transport system for blood samples in a tube system according to the method.

BACKGROUND OF THE INVENTION

It is commonly known to use conveying systems with a number of tube systems wherein items are sent from a dispatch station to a receiver station by means of vacuum or pressurised air. Typically, an elongated capsule is sent which is provided with sealing rings at each end and where the cross-section of the tube system is filled by the capsule in this way.

The capsule thereby acts as a plug which is conveyed in a long tube system. In the capsule there is typically provided the item to be transported to the desired destination. Such systems are known as so-called pneumatic dispatch systems and have been used for a long time in connection with internal post or similar in large buildings. However, by such systems there is the inexpediency that several items cannot be sent in immediate succession just like that.

This is due to the fact that the systems are closed systems and that the capsule will stop underway in the tube system if the closed system receives "false air". In order to be able to send capsules as quickly as possible in succession, various systems have been developed. Some systems have been provided with an indicator showing when a capsule arrives at the receiver station and thereby that the system is ready for use again. Also, there are variants of pneumatic dispatch system that are divided into different sections, each having its own vacuum or blowing mechanism, allowing a new capsule to be dispatched as soon as the recently dispatched capsule has passed a given position in the tube system.

However, such solutions all depend on the item to be transported to be put into a capsule and then to be dispatched. Also, it is necessary to take the item out of the capsule at the other end of the system. This means that resources are to be used both for packing items and for unpacking items. If approximately the same number of capsules are sent both ways, the problem of an accumulated number of capsules at a receiver station and a lacking number of capsules at a dispatch station is solved, but in far the most cases there will be a need for distribution of capsules to the respective dispatch stations, requiring additional resources.

EP 2483186 B1 discloses a general transport system where items can be dispatched in succession and where there is no need of providing the item in a capsule prior to dispatching, where the transport system includes a tube system with internal diameter, a dispatch station and a receiver station, and where a connection for pressurised air is provided at the dispatch station.

However, there are not specific transport systems for blood samples or methods for transporting blood samples in a tube system where the physical dimensions and/or the weight of the blood sample are/is checked, whereby it is ensured that the blood sample fits the tube system, something which may have very serious consequences for the quality of the blood samples when arriving at the receiver station.

OBJECT OF THE INVENTION

It is thus the object of the invention to indicate a method of transporting blood samples in a tube system and a transport system for blood samples in a tube system, wherein blood samples can be dispatched successively and where there is no need for placing the blood samples in a capsule before dispatching.

It is also an object of the invention to get the blood samples to the receiver station without the occurrence of haemolysis, meaning that the erythrocytes give off haemoglobin (protein), among others, to the ambient medium because the cell membrane is destroyed during the transport, e.g. by changing the osmotic pressure of the liquid in which the blood cells (erythrocytes/platelets) are situated.

It is also an object of the invention that no depreciation of the quality of the blood samples will occur due to the acceleration to which the blood samples are subjected during transport in the tube system, and which may be up to 16 times the gravitational acceleration (16 G).

There are 45% blood cells and 55% blood plasma in blood. 4-5 liters of blood contain blood cells corresponding to 25 billion erythrocytes, 35 thousand million leucocytes, and 1.5 billion platelets, and blood plasma surrounding the blood cells and consisting of 90% water corresponding to about 2 liters. Blood plasma is made from blood by centrifugation where the plasma settles at the top and the blood cells at the bottom.

When the blood samples arrives at the receiver station, typically the LD-value is measured, which is the concentration of the enzyme lactate dehydrogenase (LD) in plasma, measured as units of its catalytic activity per liter (U/L). By a rough form of transport with many jolts, the LD-value rises as a result of the inexpedient contamination of the blood plasma, and the quality of the blood samples therefore becomes worse.

DESCRIPTION OF THE INVENTION

According to a first aspect of the invention, the above mentioned object is achieved by a method of transporting blood samples in a tube system with an internal diameter that is greater than the external diameter of the applied blood samples and lesser than the lengths of the applied blood samples, as described in the introduction and in the preamble of claim 10, the method including at least the following steps:
A: a blood sample with an external diameter in the range Ø12 mm to Ø18 mm and with a length in the range from 80 mm to 110 mm is introduced in a tube system that includes a dispatch station and a receiving station, and wherein B: the blood sample is dispatched from the dispatch station by means of dispatching air,
and wherein the method further includes at least the following step between step A and step B:
A1: the physical dimensions of the blood sample are checked and it is ensured that the blood sample fits the tube system.

The ratio between the internal diameter of the tube system and the external diameter of a blood sample provides that a blood sample unhindered can be transported through the tube system, and at the same time the ratio between the internal diameter of the tube system and the length of a blood sample will prevent a blood sample from capsizing and possibly getting stuck in the tube system, which will block and prevent subsequent transport of blood samples in the tube system.

A tube system may therefor have an internal diameter in the range Ø18-Ø80 mm, though for practical, economical and space consuming reasons, among others, but also for operational reasons, it may often be more expedient to use a tube system with an internal diameter in a narrower range, as e.g. Ø18-Ø40, or even more expedient, a tube system with an internal diameter of Ø21 mm.

The method will therefore enable checking and ensuring that each individual blood sample will fit the tube system, i.e. the blood sample is neither too short nor too long, neither too thin nor too thick, and/or neither too light nor too heavy.

Since the tube system is designed to cope with bends down to a radius of 800 mm, it is therefore crucial that the individual blood sample is also of such physical nature in the form of length and thickness that the blood sample can pass through the tube system without any problems.

The tube system has an internal diameter which is greater than the largest diameter of the blood samples, e.g. at least Ø18 mm, and external diameter depending on the material of the tube system. In case of a very soft and flexible material, the material thickness of the tube may be greater than in case of a more stiff and hard material. In a preferred embodiment, the tube system has an internal diameter of Ø21 mm and an external diameter of Ø25 mm.

The blood sample is dispatched without packing into additional containers as the tube system is designed to handle the blood samples as they are, depending on the ratio between diameter and length of the individual blood sample and the diameter of the tube system, and without the blood sample breaking during transport.

If the blood sample does not have correct physical dimensions, there is a risk of breakdown in the tube system, e.g. in the form of a blockage where too large blood samples are stuck in bends or where too small blood samples are stuck across in the tube system, in particular if several blood samples run together and are wedged in the tube system.

The checking and securing is effected by a number of sensors indicating if the length of the blood sample is too short or too long. Also, a number of sensors indicate if the diameter is too small or too large.

An alternative to a sensor-controlled diameter check could be a mechanical checking where too small diameter will cause the blood sample to fall out, and where too large diameter will make the blood sample unable to get through the control and security system. This could e.g. be a frustum of a cone where blood samples with small diameters fall through and where blood samples with large diameters cannot get down into the frustum of a cone.

The blood samples are provided in an innumerable number of variants and shapes, with e.g. one or both ends being rounded or pointed, or where one end e.g. is pointed and the other end is flat. In addition, the blood samples can be aerodynamical in shape. The blood samples may also have a weight body integrated therein, that being e.g. in the form of an embedded gel at the pointed end of a blood sample or a pellet embedded in the closing mechanism. The blood samples may also be conical in shape where they e.g. are pointed at one end and flat at the other end, where the other end advantageously can be used as a pressing surface.

The blood sample check may also include vision in the form of e.g. one or more vision cameras or camera systems for use in video monitoring of the blood samples, where the video monitoring can take place in 2D and/or 3D.

In a second aspect, the present invention also concerns a method for transporting blood samples in a tube system, the method further including at least the following step between step A and step B:
A2: the weight of the blood sample is checked and it is ensured that the blood sample fits the tube system.

In case of checking the weight of the blood sample, it is a scale registering if the individual blood sample is within a suitable weight range, and thus neither too light nor too heavy for the tube system. The scale can e.g. include one or two weighing cells or weigh sensors.

If the blood sample is too light or too heavy, it can e.g. be too difficult to guide through the tube system, and even difficult to transport all the way.

In a third aspect, the present invention also concerns a method for transporting blood samples in a tube system, the method further including at least the following step between step A and step B:
A3: a bar code and/or a chip of the blood sample are/is checked, and it is ensured that the blood sample fits the tube system.

This will enable applying a bar code or a chip upon the blood sample or to embed a bar code or a chip in the blood sample itself. If bar code and chip are recognisable by the system, each individual blood sample may therefore be checked as well and thereby it will also be ensured that the blood sample in question fits the tube system.

In a fourth aspect, the present invention also concerns a method for transporting blood samples in a tube system, the method further including at least the following step between step A and step B:
A3: the amount of the blood sample is checked, and it is ensured that the blood sample fits the tube system.

This will therefore enable measuring and reading the contents of a blood sample. This may e.g. be effected by laying the blood sample on a horizontal base, or in that the blood sample stands vertically e.g. in a holder. By the reading and the knowledge of the density of the blood sample, a weight can be therefore be determined, and it may be decided if the blood sample is too light or too heavy for transport in the tube system.

In a fifth aspect, the present invention also concerns a method for transporting blood samples in a tube system, the method further including at least the following step after step B:
C: additional blood samples are dispatched in succession at random time intervals independent of the last dispatched blood sample having reached the receiving station.

This will enable transporting a plurality of blood samples in the tube system when the need arises, and without having to wait for the last dispatched blood sample reaching its destination. The transport system is designed, dimensioned and adapted for transport of blood samples without regard to how many other blood samples that otherwise are under way in the tube system.

In a sixth aspect, the present invention also concerns a method for transporting blood samples in a tube system, the method further including at least the following step between step B and step C:

B1: the pressure of the dispatching air is balanced with the dimensions and/or weight of the blood sample and with the distance over which the specific blood sample is to be transported in the tube system.

This will enable making individual considerations such that each single blood sample is dispatched at the most optimal pressure, and such that the conditions are balanced regarding the air pressure in the tube, the tube length and the dimension and/or weight of the blood sample.

If the dispatch air pressure in a tube is the same for all blood samples, irrespectively of dimensions and/or weight, the transport time for the blood samples through the tube system can vary, for which compensation can be made by adjusting the dispatch air pressure for each individual blood sample depending on dimension and/or weight.

The dispatch air pressure in a tube system with a length of 600 m may, but does not necessarily have to be the same as the dispatch air pressure in a tube system with a length of 1200 m.

In a seventh aspect, the present invention also concerns a method for transporting blood samples in a tube system, the method further including at least the following step between step B and step C:

B2: the pressure of the dispatching air is completely or partially supplemented in the tube by supplementary air, possibly by dispatching air bypassing the dispatching station, where regulating valves applied on dispatching air and supplementary air regulate the supply of the total air pressure.

This will enable supplementing the dispatch air dispatching the blood sample with a subsequent air supply to the tube system such that a desirable pressure in the tube system is present all the time.

The ratio between the dispatch air pressure and the supplementary air pressure is not necessarily the same as regulating valves at the air inlet can differentiate the pressures according to e.g. the dimension and/or weight of each individual blood sample. In a preferred embodiment, the regulating valves for pressure regulation are provided with automatic control.

The supplementary air can e.g. be air that is bypassed from the dispatch air, or it can be a separate air supply with corresponding or adapted pressure.

In an eighth aspect, the present invention also concerns a method for transporting blood samples in a tube system, the method further including at least the following step:

D: the blood sample is slowed down before the receiving station.

This will enable avoiding an abrupt deceleration of the individual blood sample by which the blood sample stops its movement instantly by contact with the delivery tray of the receiver station or similar. As abrupt decelerations will cause unwanted jolting of the individual blood samples, it is therefore desirable to avoid such abrupt decelerations, thereby maintaining the quality of the blood samples at the receiver station as well.

In an ninth aspect, the present invention also concerns a method for transporting blood samples in a tube system, wherein the method step D is produced by means of vacuum and/or by a constriction of the tube, for example by using at least two rollers/balls in the circumference of the tube and at one or more cross-sections of the tube.

This will enable slowing down the individual blood sample by e.g. creating a vacuum at the end part/section of the tube where vacuum e.g. can be formed by removing air from the tube by sucking out the tube air before the receiver station. Besides, the overpressure of the tube system can be reduced or completely removed before the receiver station through a number of openings in the tube.

Another possibility of decelerating the individual blood sample before the receiver station is constricting the tube, for example by using at least two rollers/balls in the circumference of the tube and at one or more cross-sections of the tube. The two rollers/balls thus constitute two contact points, and the tube therefore constitutes a third contact point. By disposing two rollers/balls spaced apart 120°, together with the tube there are therefore three contact points equally distributed over the circumference of the tube and in the cross-section of the tube, ensuring that the individual blood sample will be guided and thereby will not be stuck or is wedged in the system.

Another option is to provide rollers/balls all the way around in the circumference of the tube and in the cross-ssection of the tube, and preferably evenly distributed. The tube will thereby not become a contact point during the deceleration, but only the rollers/balls.

In a preferred embodiment, the balls/rollers may be spring-loaded and therefore resilient, and at the same time slowing down all blood samples allowed to be dispatched in the tube system.

An alternative to rollers and balls is a spring-loaded funnel that may open at the outlet of the funnel. In a further alternative embodiment, a function corresponding to a funnel may be constituted by slide rails/lamellae disposed conically and resiliently in the tube.

In a tenth aspect, the present invention also concerns a transport system for blood samples in a tube system, wherein the transport system includes at least a tube system with a dispatch station and a receiver station, the dispatch station having at least one connection for dispatching air and the receiver station having at least one braking function, and wherein the transport system is provided with blood sample control and security means.

This will enable dispatching blood samples within a predetermined dimensional range and/or weight range in succession, and where it is thus ensured that each single blood sample fits the tube system, where there is no need for providing the blood samples in a capsule before dispatching, and where the blood samples can be transported through the tube system without risk of occurrence of haemolysis or other depreciation of the quality of the blood samples.

In a preferred embodiment, the tube system is made of a polymer but may alternatively be made of other materials, however preferably materials with corresponding properties. In a preferred embodiment, the tube has an internal diameter of Ø21 mm and an external diameter of Ø25 mm.

In an eleventh aspect, the present invention also concerns a transport system for blood samples in a tube system, wherein the internal surface of the tube system is smooth and where possible bending radii are at least 800 mm.

This will enable transporting blood samples by sliding movement and so that each blood sample, due to the smooth tubes, will not be subjected to impacts and vibrations, and such that the blood quality is maintained (even at 16 G), i.e. the blood sample will not break and no haemolysis will occur.

By providing bending radii of at least 800 mm in tube systems with internal smooth surfaces it is ensured that no depreciation of the quality of the blood samples will occur due to jolting provoked by tube joints or similar transitions.

In an twelfth aspect, the present invention also concerns a transport system for blood samples in a tube system, the transport system further including at least one bypass channel bypassing the dispatch station.

This will enable supplementing the dispatch air dispatching the individual blood sample with a subsequent air supply to the tube system such that a desirable pressure in the tube system is present all the time, where the air inlets can differentiate the pressures and where a bypass channel e.g. can be air that is bypassed from the dispatch air.

In an thirteenth aspect, the present invention also concerns a transport system for blood samples in a tube system, the transport system further including a mechanical suction device immediately before the receiver station.

This will enable slowing down the individual blood sample by e.g. sucking air out of the tube system and discharging the air.

DESCRIPTION OF THE DRAWING

The invention will now be explained more closely in the following by description of non-limiting embodiments with reference to the drawing, where:

FIG. 1 shows an example of a transport system.

LIST OF DESIGNATIONS 1 transport system
2 tube system
3 dispatch station
4 receiver station
5 blower
6 revolving drum
7 recess
8 blood sample
9 centre axis
10 connection channel
11 air flow regulator
12 openings
13 displaceable part
14 suction device
15 delivery tray
16 blood sample checking and security means

DETAILED DESCRIPTION OF EMBODIMENTS OF THE INVENTION

In FIG. 1 appears a transport system 1 according to the invention in a schematically shown embodiment, where the transport system 1 includes a tube system 2 which extends from a dispatch station 3 to a receiver station 4. Under the dispatch station 3 appears a blower 5 from where a sufficient amount of air is blown into the tube system 2.

The air is conducted through the dispatch station 3, which in the shown example is provided with a revolving drum 6 with a number of recesses 7. When a blood sample 8 has passed the blood sample checking and security means 16 and therefore is allowed, the blood sample 8 is then placed a recess 7, and by rotating the revolving drum 7 about its centre axis 9, the recesses 8 may be brought one by one into the airflow present in the tube system 2. In order to ensure a sufficient excess of air in the tube system 2, supplementary air is conducted via a bypass or connection duct 10 after the dispatch station 3 by which it is ensured that blood samples 8 underway in the tube system 2 remain in movement.

Immediately after dispatching a blood sample 8 from the dispatch station 3, the speed of the blood sample 8 can be regulated by an airflow regulator 11 which operates by discharging a part of the air through openings 12 in the tube system 2. The speed of the blood sample 8 is hereby reduced after being accelerated to a suitable speed after the dispatch station 3.

In the shown embodiment of the airflow regulator 11, there are openings 12 in the tube system 2 which may be covered more or less by a displaceable part 13. In order to further reduce the speed of the blood sample 8 before the blood sample 8 arrives at the receiver station 4, in the shown transport system 1 there is depicted yet an airflow regulator 11, and also a suction device 14 by which air can be removed.

By closing and removing part of the air with the airflow regulator 11 and even more by the suction device 14, the blood sample 8 can be decelerated to such a degree that the blood sample 8 comes to rest in a delivery tray 15.

The invention claimed is:

1. A method of transporting blood samples in a tube system comprising:
   providing the tube system with an internal diameter that is greater than the external diameter of the blood samples and lesser than the lengths of the blood samples, the method including at least the following steps:
   A: a blood sample with an external diameter in the range Ø12 mm to Ø18 mm and with a length in the range from 80 mm to 110 mm is introduced in the tube system having a diameter greater than Ø18 mm up to Ø80 mm and that includes a dispatch station and a receiver station, and wherein
   B: the blood sample is dispatched from the dispatch station by means of dispatching air, wherein the method further includes at least the following step between step A and step B:
   A1: the physical dimensions of the blood sample are checked prior to dispatching the blood sample from the dispatch station wherein a diameter and/or a length of the blood sample is determined with one or more of the following:
      i. one or more sensors, and/or
      ii. mechanical checking, and/or
      iii. one or more vision cameras or camera systems,
   thereby indicating if the length of the blood sample is too short or too long and/or if the diameter of the blood sample is too small or too large to ensure that the blood sample fits in the tube system and to prevent the blood sample from capsizing in the tube system, and
   discarding from the dispatch station blood sample units outside predefined ranges of dimensions of the blood sample units selected from length, diameter, and combinations thereof, thereby excluding discarded blood sample units from being transported and causing blockage in the system.

2. A method for transporting blood samples in a tube system according to claim 1, wherein the method further includes at least the following step between step A and step B:
   A2: the weight of the blood sample is checked and it is ensured that the blood sample fits the tube system.

3. A method for transporting blood samples in a tube system according to claim 1, wherein the method further includes at least the following step between step A and step B:

A3: a bar code and/or a chip of the blood sample are/is checked.

4. A method for transporting blood samples in a tube system according to claim 1, wherein the method further includes at least the following step between step A and step B:

A3: the amount of the blood sample is checked.

5. A method for transporting blood samples in a tube system according to claim 1, wherein the method further includes at least the following step after step B:

C: additional blood samples are dispatched in succession at random time intervals independent of the last dispatched blood sample having reached the receiver station.

6. A method for transporting blood samples in a tube system according to claim 1, wherein the method further includes at least the following step between step B and step C:

B1: the pressure of the dispatching air is balanced with the dimensions and/or weight of the blood sample and with the distance over which the specific blood sample is to be transported in the tube system.

7. A method for transporting blood samples in a tube system according to claim 1, wherein the method further includes at least the following step between step B and step C:

B2: the pressure of the dispatching air is completely or partially supplemented in the tube by supplementary air.

8. A method for transporting blood samples in a tube system according to claim 1, wherein the method further includes at least the following steps:

D: the blood sample is slowed down before the receiver station.

9. A method for transporting blood samples in a tube system according to claim 8, wherein the method step D is produced by means of vacuum and/or by a constriction of the tube.

10. A transport system for blood samples in a tube system according to the method according to claim 1, wherein the transport system includes at least the tube system comprising an internal diameter greater than an external diameter of blood sample units and lesser than lengths of the blood sample units, wherein the tube system further comprises a dispatch station and a receiver station, the dispatch station having at least one connection for dispatching air and the receiver station having at least one braking function, and wherein the transport system is provided with blood sample control and security means to exclude blood sample units outside predefined ranges of physical dimensions of length and/or diameter of the blood units from transport in the system, and wherein the dispatch station comprises a sample control unit for detecting the physical dimensions of the blood sample and discarding the blood sample units having the physical dimensions outside the predefined ranges prior to dispatching the blood sample units from the dispatch station, and wherein the blood sample control unit comprises one or more monitoring systems for checking a diameter and/or length of the blood sample means selected from one or more of the following:

i. one or more sensors,
ii. mechanical checking,
iii one or more vision cameras or camera systems with 2D and/or 3D detection.

11. A transport system for blood samples in a tube system according to claim 10, wherein the internal surface of the tube system is smooth and possible bending radii are at least 800 mm.

12. A transport system for blood samples in a tube system according to the method according to claim 10, wherein the transport system includes at least one bypass channel bypassing the dispatch station.

13. A transport system for blood samples in a tube system according to the method according to claim 10, wherein the transport system further includes a mechanical suction device immediately before the receiver station.

14. A method for transporting blood samples in a tube system according to claim 7, wherein in step B2:

the pressure of the dispatching air is completely or partially supplemented in the tube by supplementary air by dispatching air bypassing the dispatch station, where regulating valves applied on dispatching air and supplementary air regulate the supply of the total air pressure.

15. A method for transporting blood samples in a tube system according to claim 9, wherein the method step D is produced by means of vacuum and/or by a constriction of the tube by using at least two rollers/balls in the circumference of the tube and at one or more cross-sections of the tube.

* * * * *